US010413358B2

(12) United States Patent
Mulrooney

(10) Patent No.: US 10,413,358 B2
(45) Date of Patent: Sep. 17, 2019

(54) MULTI-FUNCTIONAL CATHETER

(71) Applicant: PHAGENESIS LIMITED, Ledbury (GB)

(72) Inventor: Conor Mulrooney, Stockport Cheshire (GB)

(73) Assignee: PHAGENESIS LIMITED, Ledbury (GB)

(*) Notice: Subject to any disclaimer, the term of this patent is extended or adjusted under 35 U.S.C. 154(b) by 65 days.

(21) Appl. No.: 15/462,219

(22) Filed: Mar. 17, 2017

(65) Prior Publication Data
US 2017/0189110 A1 Jul. 6, 2017

Related U.S. Application Data

(63) Continuation of application No. 14/009,195, filed as application No. PCT/GB2012/000288 on Mar. 30, 2012, now abandoned.

(30) Foreign Application Priority Data

Apr. 1, 2011 (GB) .................................. 1105622.3

(51) Int. Cl.
A61B 18/14 (2006.01)
A61B 1/05 (2006.01)
(Continued)

(52) U.S. Cl.
CPC .......... *A61B 18/1492* (2013.01); *A61B 5/037* (2013.01); *A61B 5/0492* (2013.01);
(Continued)

(58) Field of Classification Search
CPC .. A61M 2025/0226; A61M 2025/0004; A61M 2025/0002; A61M 25/00;
(Continued)

(56) References Cited

U.S. PATENT DOCUMENTS 4,381,011 A 4/1983 Somers, III
4,531,937 A 7/1985 Yates
(Continued)

FOREIGN PATENT DOCUMENTS

CN 2873126 2/2007
CN 101836891 9/2010
(Continued)

OTHER PUBLICATIONS

International Search Report for PCT/GB2012/000288, Completed by the European Patent Office dated Jun. 22, 2012, 5 Pages.

*Primary Examiner* — Boniface N Nganga
(74) *Attorney, Agent, or Firm* — Brooks Kushman P. C.

(57) ABSTRACT

A catheter suitable for delivering an electric current to the body, in particular a catheter having electrodes that can be positioned independently of the main elongate shaft of the catheter. More particularly the catheters include a movable sleeve that incorporates the electrodes. A movable sleeve includes one or more electrodes and advances in the construction of the electrodes and related components is disclosed. Methods for positioning electrodes at a treatment site in the body for diagnostic or therapeutic applications, particularly electrical pharyngeal stimulation are also disclosed.

18 Claims, 7 Drawing Sheets

(51) Int. Cl.
*A61B 5/00* (2006.01)
*A61B 5/145* (2006.01)
*A61J 15/00* (2006.01)
*A61M 25/00* (2006.01)
*A61B 5/03* (2006.01)
*A61B 5/0488* (2006.01)
*A61N 1/05* (2006.01)
*A61B 5/0492* (2006.01)
*A61B 5/08* (2006.01)

(52) U.S. Cl.
CPC ............ *A61B 5/04884* (2013.01); *A61B 5/08* (2013.01); *A61B 5/14539* (2013.01); *A61B 5/6852* (2013.01); *A61J 15/0026* (2013.01); *A61J 15/0084* (2015.05); *A61M 25/00* (2013.01); *A61N 1/05* (2013.01); *A61N 1/0517* (2013.01); *A61M 2025/0002* (2013.01); *A61M 2025/0004* (2013.01); *A61M 2025/0006* (2013.01); *A61M 2025/0008* (2013.01)

(58) Field of Classification Search
CPC .. A61N 1/0517; A61N 1/0519; A61N 1/3601; A61N 1/36007; A61B 5/08; A61B 5/0492; A61B 5/04884; A61B 5/037; A61B 5/6852; A61B 18/1492; A61J 15/0084

See application file for complete search history.

(56) References Cited

U.S. PATENT DOCUMENTS

| | | |
|---|---|---|
| 4,960,412 A | 10/1990 | Fink |
| 5,109,870 A | 5/1992 | Silny et al. |
| 5,125,904 A | 6/1992 | Lee |
| 5,928,163 A | 7/1999 | Roberts et al. |
| 6,048,340 A | 4/2000 | Miyagi |
| 6,259,938 B1 | 7/2001 | Zarychta et al. |
| 6,544,226 B1 | 4/2003 | Gaiser et al. |
| 6,733,500 B2 | 5/2004 | Kelley et al. |
| 6,771,996 B2 | 8/2004 | Bowe et al. |
| 7,435,248 B2 | 10/2008 | Taimisto et al. |
| 7,871,430 B2 | 1/2011 | Pavcnik et al. |
| 8,092,433 B2 | 1/2012 | Hamdy |
| 8,454,597 B2 | 6/2013 | Scopton et al. |
| 2001/0093413 | 11/2001 | Bowe |
| 2002/0165537 A1 | 11/2002 | Kelley et al. |
| 2002/0177765 A1 | 11/2002 | Bowe et al. |
| 2005/0192559 A1* | 9/2005 | Michels ............ A61M 39/1011 604/533 |
| 2005/0209581 A1 | 9/2005 | Butts |
| 2006/0173407 A1* | 8/2006 | Shaughnessy ..... A61B 1/00158 604/95.01 |
| 2008/0249507 A1 | 10/2008 | Hadani |
| 2009/0275825 A1 | 11/2009 | Thomas |
| 2010/0030133 A1* | 2/2010 | Elia ....................... A61B 5/037 604/28 |
| 2010/0174170 A1 | 7/2010 | Razavi |
| 2010/0241118 A1 | 9/2010 | Akahane |
| 2013/0103034 A1 | 4/2013 | Chanduszko et al. |

FOREIGN PATENT DOCUMENTS

| | | |
|---|---|---|
| JP | H11503041 | 3/1999 |
| JP | 2003526460 | 9/2003 |
| JP | 2005523124 | 8/2005 |
| JP | 2007506515 | 3/2007 |
| JP | 2007519489 | 7/2007 |
| JP | 2007535972 | 12/2007 |
| WO | 2006024825 | 3/2006 |
| WO | 2007129002 | 11/2007 |
| WO | 2010023579 | 3/2010 |

* cited by examiner

MULTI-FUNCTIONAL CATHETER

CROSS-REFERENCE TO RELATED APPLICATIONS

This application is a continuation of U.S. application Ser. No. 14/009,195 filed Nov. 13, 2013, which is the U.S. national phase of PCT Application No. PCT/GB2012/000288 filed on Mar. 30, 2012, which claims priority to Great Britain Patent Application No. 1105622.3 filed on Apr. 1, 2011, the disclosures of which are incorporated in their entirety by reference herein.

BACKGROUND

The present invention relates to novel catheters suitable for delivering an electric current to the body, in particular to catheters that have electrodes that can be positioned independently of the main elongate shaft of the catheter. More particularly the invention relates to catheters that include a movable sleeve that incorporates the electrodes. It also relates to a movable sleeve that includes one or more electrodes and to advances in the construction of the electrodes and related components. The invention also relates to methods for positioning electrodes at a treatment site in the body for diagnostic or therapeutic applications.

Catheters that include electrodes that are used for diagnosis, measuring and other medical applications are well known, catheters comprising multiple electrodes, for example, see U.S. Pat. No. 5,109,870 Silny. Whilst catheters comprising electrodes are known in the art, they suffer from a number of disadvantages.

International patent publication No. WO 2006/024825 (Hamdy) discloses a catheter for assisting recovery from dysphagia including a catheter for insertion into the body of a patient via the mouth or nose, a particularly useful application of the devices of the present invention. The electrodes are in the elongate shaft of the catheter such that when the catheter is in a suitable position within the patient's body, the electrodes are in a position to apply electrical pharyngeal stimulation.

The present inventors have, however, found that accurate positioning of the catheter disclosed in Hamdy can be problematic. The catheter is required to fulfil two functions—firstly to safely and effectively deliver nutrition to the patients' stomach via an internal lumen of the elongate shaft of the catheter and secondly to deliver electrical stimulation to a defined region of the oropharynx via electrodes on the outer surface of elongate shaft of the catheter. The incorporation of both functions into the main body of the catheter has advantages, it minimises patient discomfort and is consistent with existing standards of care in that it replaces a conventional nasogastric (NG) feeding tube and can be introduced into the patient in the same way as a conventional NG tube.

The fixed position of the electrodes has, however, been found by the inventors to have some disadvantages. The catheter must be inserted into the patient so that the distal end is correctly positioned in the stomach to meet the requirement to safely and effectively deliver nutrition. The correct insertion distance can vary considerably dependent on the height of the patient and can routinely be different by 20 cm or more from patient to patient. In contrast, the optimal position for the electrodes in the oropharynx is within a 2-3 cm vertical distance range. Thus, in order to ensure that 5 the electrodes on the elongate shaft of the catheter are correctly positioned there must either be a range of catheter sizes to accommodate the variation in patient height, or the catheter must be designed to be sufficiently long for the tallest anticipated patient and then over inserted into shorter patients in order to bring the electrodes into the correct position. This introduces risks that the distal end of the catheter does not remain in the stomach but continues into the duodenum, becomes entangled in the stomach preventing effective nutrition delivery or easy removal, or re-emerges from the stomach into the lower oesophagus.

The fixed positioning of both electrical stimulation and nutrition functions in the invention of Hamdy et al. also has the disadvantage that, in the event the internal lumen of the catheter becomes blocked with nutritional feed in a way that cannot be resolved, the entire catheter must be replaced.

In addition, it has become apparent that once the treatment with electrical stimulation has been completed it may still be necessary to keep the catheter in place solely for the purposes of enteral nutrition. This is not desirable from a patient comfort or safety management perspective. It would be particularly advantageous for these reasons to be able to remove the electrical stimulation functionality, whilst leaving the nutrition delivery functionality in place.

SUMMARY

The present inventors have now determined that a catheter that comprises the electrodes in a separate, movable electrode carrying component provides significant advantages to the accurate positioning of electrodes that are used to deliver electric current to the body. Thus the present invention provides a catheter for delivering an electrical stimulus to the body comprising an elongate shaft; a sleeve incorporating one or more electrodes, the sleeve being movable along the elongate shaft such that the position of the sleeve is adjustable; and a means to fix the sleeve to the elongate shaft once the sleeve is in position.

Thus the present invention provides advantages over current catheter designs by permitting the incorporation of more than one function into a single catheter and allowing each of the functions to be independently positioned and optimised. Thus the catheter comprises an elongate shaft that may incorporate at least one therapeutic or diagnostic function. The catheter may thus comprise at least one diagnostic or therapeutic function in both the elongate shaft and the sleeve. The elongate shaft may have a therapeutic function such as the provision of enteral nutrition, and the sleeve has electrical stimulation electrodes. The catheter may incorporate other diagnostic functions such as pressure or pH sensors.

The catheter of the present invention may also be configured such that it allows for selective removal of certain functional components once they are no longer required, or in the event that their functionality becomes compromised. For example, the catheter can be configured such that the electrode carrying sleeve can remain in the body when the elongate shaft is removed.

It is also possible to configure the catheter such that the sleeve can be removed leaving the elongate shaft in the body.

Examples of catheters according to the present invention that incorporate more than one function include:

A catheter for electrical stimulation comprising a sleeve with electrodes for the delivery of a stimulus and an elongate shaft with sensors to detect the effect of the stimulus delivered. Thus the catheter combines an electrical stimulation function in the sleeve and a diagnostic function in the elongate shaft to measure the effect of the stimulus. Such a catheter may be configured such that the elongate shaft is movable. This allows the effect of the stimulus to be assessed at a number of different positions without moving the point of stimulation. Alternatively the point of stimulation can be moved by moving the sleeve.

A catheter for the delivery of electrical stimulation comprising a sleeve with one set of stimulating electrodes and an elongate shaft with a second set of stimulating electrodes. This would have the advantage of allowing the distance between stimulation points to be adjusted as required but also keeping one stimulation point fixed if needed.

A catheter for measurement comprising a sleeve incorporating electrodes wherein the electrodes are sensors to measure for example pressure, EMG signals or pH and a core elongate structure with sensors to measure for example pressure, EMG signals or pH. This arrangement would provide the possibility to measure the same parameters at a fixed and user controlled variable location simultaneously or measure two different parameters at a fixed and user controlled variable location simultaneously. One example of a useful application using this arrangement would be the measurement of lower oesophageal sphincter strength and separately the measurement of pH at multiple points along the oesophagus.

A catheter for the delivery of electrical stimulation and the measurement of pressure, comprising a sleeve that incorporates one or more electrodes to deliver electrical stimulation, and an elongate shaft incorporating pressure sensors. The pressure sensors can be positioned on the elongate shaft such that they can be used to measure upper oesophageal sphincter pressure. This arrangement would help to inform the user whether the distal end of the catheter was in the upper airway or in the oesophagus by virtue of pressure readings from the upper oesophageal sphincter and facilitate the correct placement of stimulation electrodes in the pharynx or oesophagus rather than in the airways.

A catheter in the form of a two part catheter for the delivery of electrical stimulation and measurement of pH comprising a sleeve with electrodes to deliver electrical stimulation and a core elongate structure that was capable of extending as far as the patients' stomach and incorporating pH sensors at its distal end. This arrangement would help to inform the user whether the distal end of the catheter was in the airways or in the oesophagus by virtue of pH readings from the patients' stomach and facilitate the correct placement of stimulation electrodes in the pharynx or oesophagus rather than in the airways.

Another example would be a catheter for the delivery of electrical stimulation and nutrition, comprising a sleeve with electrodes to deliver electrical stimulation and an elongate shaft in the form of a nasogastric feeding tube. This catheter could be used to treat dysphagia, particularly acute dysphagia, whilst also maintaining a safe supply of nutrition to the patients' stomach.

Thus the catheter of the present invention may be a pharyngeal stimulation catheter for the treatment of acute or chronic dysphagia.

Dysphagia is the condition whereby a patient has difficulty in swallowing, or is unable to swallow. Dysphagia may be caused, for example, by stroke, neurodegenerative diseases, and brain tumours or in some cases by other co-morbidity such as respiratory disorders. Dysphagia may be an acute condition arising due to acute neurological damage following stroke or traumatic brain injury (TBI) and managed in a hospital setting. Dysphagia may also be a persistent or chronic condition (defined as remaining present for periods greater than 6 weeks after initial onset). This could be due to non-recovery from a stroke or TBI induced deficit, it could be a feature of a progressive neurodegenerative disease such as Parkinson's disease or it could be a feature of a condition such as cerebral palsy or multiple sclerosis. In this case management is most often outside of a hospital setting. Dysphagia, whether acute or chronic, is a life threatening condition primarily due to the development of respiratory infections arising from the uncontrolled entry of food and liquids into the airways. Dysphagia after stroke carries a six-fold increase of aspiration pneumonia by comparison with stroke patients without dysphagia.

It is envisaged that a pharyngeal stimulation catheter according to the present invention may have several, different configurations depending whether it is for the treatment of patients with an acute dysphagia or chronic dysphagia. For example where a patient is presenting with dysphagia post stroke in an acute care hospital environment it is likely the patient will also require nutrition delivery via an enteral feeding tube. A configuration of the device to combine nutrition delivery capability with the ability to also delivery therapeutic electrical stimulation to the pharynx is therefore particularly advantageous for an acute dysphagia patient. It is envisaged that this configuration of the catheter for treatment of dysphagia and for nutrition delivery will used in a hospital environment, will incorporate a feeding tube and be in place for relatively long periods of time (up to 29 days). An alternative configuration particularly suited to treating patients with chronic dysphagia would not require the incorporation of an enteral feeding tube but would have different functional requirements reflecting the context of care i.e., potentially community based rather than in a hospital setting. The main function of the elongate shaft in this case would be to facilitate placement of the electrode carrying sleeve at the treatment site.

In the configurations where the elongate shaft is a nasogastric (NG) tube the elongate shaft may incorporate a visual position indicator on its external surface. The elongate shaft may also include connectors suitable for engagement with an enteral feeding set.

However, as will be apparent to the skilled man, and as described above, it is envisaged that the catheters of the present invention, will be useful in other therapeutic or diagnostic applications, particularly when it is desirable to adjust the position of the electrodes relative to the position of the elongate shaft and or to accurately position electrodes at a treatment or diagnostic site.

Examples of the kind of functionality that may be incorporated into the elongate shaft or the sleeve of the catheter include but are not limited to electrodes, sensors, transducers, wires, conducting materials, active chemical surface coatings, lubricants, balloons or stents.

The sleeve is dimensioned to permit it to move with respect to the elongate shaft. The sleeve may be dimensioned such that when the catheter is in position in the body the sleeve extends to the outside of the body. This is advantageous as it permits the position of the sleeve to be adjusted from outside the body. It also means that the sleeve can be positioned by the health care professional without the need for a separate mechanism in the catheter to deploy or adjust the sleeve. Thus the sleeve position can be adjusted manually.

Typically, the sleeve is a substantially transparent flexible tube made of polyurethane, PVC, polyamide, silicone or equivalent material. The sleeve is dimensioned to permit it to move with respect to the elongate shaft, thus it is sized to have a larger internal diameter than the external diameter of the elongate shaft. For example, if the elongate shaft is an adult nasogastric feeding tube, the dimensions of the sleeve will be approximately 5 mm in outer diameter, with an internal lumen of approximately 3 mm diameter and for approximately 35-45 cm in length. This arrangement is particularly suitable for a pharyngeal stimulation catheter for the treatment of acute dysphagia. It will be apparent to the skilled man that the dimensions of the sleeve may vary depending on the patient population to be treated. For example, the feeding tube may be 8F and the sleeve 14F.

The sleeve may incorporate one or more pairs of ring electrodes and conducting elements disposed laterally along the walls of the sleeve connected to the electrodes. The walls of the sleeve may include pre-formed lumen for the conducting elements (wires). Thus the sleeve may be formed by multi-lumen extrusion. The sleeve may then be constructed by inserting the wires into the appropriate lumen. The wires may be coated with an insulating material such as FEP (Fluorinated ethylene propylene) or the like.

The sleeve may also include a device, for example a Y connector, to guide the wires to an electrical connector.

The sleeve may be adapted to help it to slide over the elongate shaft. The sleeve and/or elongate shaft may be modified by coating with a lubricant, by modification of surface hardness, by incorporation of surface features, or otherwise to allow free relative movement of sleeve along the length of the elongate shaft both whilst outside and inside the patient.

The internal surface of the sleeve may be modified with respect to its hardness, shape, finish or coating such that the modification helps to minimise friction when the sleeve is placed or moved along the elongate shaft on which it is positioned.

The sleeve may have a position indicator, for example a visual indicator such as printed guide or window on its surface to facilitate its positioning relative to the elongate shaft.

It is possible to configure the catheter such that the sleeve can be removed leaving the elongate shaft in the body. Such an arrangement is particularly advantageous in the treatment of acute dysphagia, where the elongate shaft functions as a feeding tube.

A further feature of the invention is wherein the distal end of the sleeve is shaped to minimise patient discomfort. This shaping may comprise a graduated or rounded end to ensure the sleeve does not disturb the tissue during insertion or removal.

An important feature of the present invention is that the provision of a separate sleeve and elongate shaft allows a single catheter to be used where otherwise two or more might be required. In addition the present invention provides a catheter comprising movable sleeve and elongate shaft and a position indicator, the position indicator providing a means to accurately position the catheter in the body.

Thus the catheter according to the invention may include a position indicator arranged to indicate when the sleeve is correctly positioned on the elongate shaft. Typically the sleeve includes a position indicator; however, it may be advantageous if both the sleeve and the elongate shaft include a position indicator. The catheter may comprise a position indicator arranged to indicate when the sleeve is located correctly in respect of the elongate shaft and is thus in a predetermined position within a patient.

Position indicators according to the present invention may comprise visible markings on an exterior surface of the sleeve and/or elongate shaft, such as a guide or scale on a surface of the sleeve to indicate vertical and/or lateral placement. The guide or scale may provide a number of indicators depending on the patient to be treated, for example, male or female and vertical distance ranges based on patient height. Such guides or scales may be based on placement of the sleeve. In a preferred embodiment there is a printed window on the sleeve which lines up with a printed guide on the elongate shaft identifying the insertion distance. For example, in a pharyngeal stimulation catheter configured for acute use, the distance from the windows to the electrodes will be in the range of 14 cm and 17 cm to ensure that the electrodes will be in the correct position within the patient when the catheter is inserted. The catheter may incorporate more than one position indicator, for example, more than one window which may optionally be colour coded to cater for the different applications and sizes of patient or the route of catheter insertion (oral or nasal).

It will be apparent to one skilled in the art that the position indicators may be combined with other catheter functions that provide diagnostic information to facilitate correct placement of the electrodes. For example a catheter for pharyngeal stimulation may incorporate a position indicator in the form of a visual guide on the sleeve and/or elongate shaft and also a pressure sensor to detect the high pressure zone in the upper oesophagus sphincter of the patient. The pressure sensor may be incorporated into the sleeve or the elongate shaft of the catheter. Other suitable sensors include $CO_2$, moisture content or pH sensors.

The catheters of the present invention have a sleeve that can move relative to the elongate shaft, the catheter also having a means to fix the sleeve in position. It may be advantageous if this fixing means is reversible. Thus after the sleeve is fixed in position on the elongate shaft it is still possible to release the fixing means to make further adjustments to the position of the sleeve and/or remove the sleeve or elongate shaft. The fixing means may be engaged before or after insertion into the patient. Advantageously, the fixing means is located at the proximal end of the sleeve.

The fixing means, for example in the form of a clip, may form part of the sleeve or be mounted thereon. The fixing means may be positioned at the proximal end of the sleeve. However, particularly for a pharyngeal stimulation application, the fixing means may be in the form of a clip that is located externally of the body, i.e. at the proximal end of the sleeve/elongate shaft, when the catheter is in position in the body. Thus the catheter of the invention comprises a clip for fixing the position of the sleeve relative to the elongate shaft, said clip being located at the proximal end of the catheter.

Ideally the fixing means also functions to seal any gaps between the sleeve and elongate shaft, for example, when the clip is located at the proximal end of the sleeve, to prevent liquid or material ingress between the sleeve and the elongate shaft.

When not fixed in position the sleeve is capable of freely moving along the length of the elongate shaft. Advantageously, the fixing means may be positioned at the proximal end of the sleeve and thus may remain accessible to the operator when the catheter is inserted into the body. The fixing means, may form part of a Y-connector assembly and therefore part of the sleeve if the sleeve incorporates a Y-connector, For example, the proximal end of the sleeve may be attached to a connector, which incorporates the fixing means, the fixing means acting on the elongate shaft, e.g. NG tube, to secure the position of the sleeve relative to the elongate shaft. This permits the user to move the shaft relative to the sleeve and then engage the fixing means to secure the sleeve. The connector may also incorporate a conduit to guide the wires to a suitable electrical connector.

The connector may be in the form of a Y-connector as discussed above. An example of such a connector arrangement is shown in FIG. 5.

Alternatively, the fixing means may be a feature independent of but connectable to a Y-connector.

The fixing means may take the form of a reversibly engageable clip fixed to the sleeve and capable of gripping the elongate shaft, for example by virtue of ridges or equivalent on its inner surface. It may also operate in a similar fashion to a Touhy-Borst valve whereby a connector on the sleeve contains a deformable O-ring which can be reversibly compressed. In this way it is possible to hold or release the elongate shaft which runs through the centre of the O-ring. The reversibly engageable clip or fixing means may also take the form of a collet that grips the elongate shaft, or interference ribs or wave form that grip the shaft.

The fixing means may engage with the elongate shaft to fix the position of the sleeve. The fixing means may include resiliency deformable materials such as deformable silicone or the like. The fixing means may be fabricated from this type of material, for example, in the form of compliant silicone grommet. Alternatively, the deformable material may be used to coat the portions of the fixing means that engage with the elongate shaft, particularly if the elongate shaft is an NG feeding tube. If a deformable material such as a silicone or equivalent is used it can have two useful features—it deforms to spread the applied load and it creates friction such that the applied load can theoretically be less. These are both advantageous as a uniform loading and lower applied pressure reduces the chance that the feeding tube gets deformed and the cross sectional area of the lumen is compromised (leading to increased risk of blockage).

Thus the fixing means, particularly a reversible fixing means, may comprise a resiliency deformable material, for example a deformable silicone or the like. The fixing means may be formed from or coated with the resiliently deformable material.

Catheters according to the present invention may also include means for connecting said electrodes to a power supply such as the wiring junction, for example, in the form of a Y-connector or the like, as described above. The means for connecting may be incorporated into the fixing means. In a catheter used for pharyngeal stimulation this facilitates removal of all of the electrical stimulus components upon removal of the sleeve.

Thus the catheter according to the present invention may comprise an elongate shaft, a sleeve incorporating one or more electrodes, the sleeve being movable along the elongate shaft such that the position of the sleeve is adjustable; and a reversible means to fix the sleeve to the elongate shaft once the sleeve is in position, the sleeve being attached at its proximal end to a connecter and the connector including a means for connecting the electrodes to a power supply and the means for fixing in the form of a reversible fixing means capable of gripping the elongate shaft to fix the sleeve to the elongate shaft once the sleeve is in position.

The invention also provides advances in the incorporation of electrodes into catheters by significantly improving the configuration of the electrode components into a device for insertion to the body.

In a further aspect, the sleeve comprises multi-strand conducting elements extending along a length of the sleeve and terminating in at least one electrode. Particularly the multi-strand conducting element comprises steel. More particularly, the conducting element is a multi-strand steel wire.

In the past, single stranded copper wire has been utilised in catheters, however, the inventors have discovered that copper wire can have a number of significant disadvantages. Particularly, conventional copper wire is not robust enough at the appropriate diameter and when arranged so that is attached to the surface of the sleeve may easily detach from the surface of the tube leading to puncture hazard. It also breaks more easily, leading to failure of the electrode. In addition, copper is more malleable meaning that the wire exhibits differential stretching causing bunching or, again, wire detachment. However, insulated copper wire may be used, particularly if inserted into a lumen in the wall of the sleeve. Thus the catheter according to the present invention may comprise a sleeve with a wall incorporating moulded lumen carrying wires to the electrodes.

Multi-strand steel coiled wire is strong and more rigid with a reduced risk of beading or bunching and breakage. Such wire adapts to the curvature of the anatomy and negates the requirement for a separate guide wire. Surprisingly, when co-extruded, the adhesion between the steel wire and the sleeve is stronger or greater than that of a comparable copper wire. Multi-strand wire means that each electrode comprises more individual connections—if one wire fails, the electrode continues to function.

The inventors have identified a multiplicity of advantages in using multi-strand steel wire over more commonly used copper wires for these applications, specifically;

The wires confer greater rigidity to the sleeve enhancing the process of catheter insertion.

Locating the wires on either side of the sleeve confers directional conformity to the catheter (i.e., the sleeve will only easily bend in one plane) and therefore simplifies printing and use of surface guides.

The multi-strand steel wire is considerably stronger and forms a better bond with the sleeve walls than copper. These features significantly reduce the risk of wire breakage, leading to product fault or puncture injury to the patient, and also prevent differential stretching of wire and sleeve walls leading to bunching or wire detachment.

This inventive concept therefore has application in either a novel sleeve according the present invention or may be incorporated into a more traditional catheter. In a further aspect of the present invention there is provided a catheter for delivering an electrical stimulus to the body comprising a sleeve adapted to move over an elongate shaft wherein the sleeve comprises multi-strand conducting elements extending along a length of the sleeve and terminating in at least one electrode, the wire may be multi-strand steel wire.

In another independent aspect there is provided a catheter comprising multi-strand steel conducting elements extending along a length of the catheter and terminating in at least one electrode.

The catheter as described above may be used for delivering an electrical stimulus to the body comprising applying electrical pulses capable of inducing stimulation to electrodes located on the surface of an elongate shaft or sleeve, the catheter being inserted into the body of a patient and the electrodes being located in a position suitable for applying electrical stimulation to the target tissue or organ.

The catheter of the present invention has significant advantages over the known devices and solves many of the problems associated with them. In particular the device is well adapted for the incorporation of nasogastric feeding tubes.

Firstly it separates nutritional and stimulation functionality to allow both to be positioned optimally on a per patient basis. This separation also allows the nutrition component to be removed and replaced if required (due to blockage) whilst retaining the stimulation component located on the sleeve within the body. Leaving the sleeve in the body is advantageous in that it facilitates replacement of the feeding tube by providing a conduit or guide to aid introduction of the tube. This greatly simplifies the procedure for replacing the tube as there is virtually no risk of accidentally inserting the tube into the airways. It also means that the final position of the NG tube need not be confirmed by X-ray. The presence of the sleeve also aids accurate vertical positioning of the replacement tube.

Separate nutritional and stimulation functionality also allows for the stimulation function, i.e. electrode carrying sleeve, to be removed from the patient on completion of electrical treatment, whilst the feeding tube remains in position in the patient.

One of the primary design challenges for a catheter intended to be used to deliver an electrical stimulation inside the body is to identify mechanisms to safely and easily introduce the sleeve and in particular the electrodes to the correct location in a manner most easily tolerated by the patient. Simple controls and confirmatory feedback should provide confidence to users that the device has been safely and successfully positioned. The device once placed should be secure, as comfortable as possible and capable of supporting minor adjustments to maximise electrode contact in the correct location.

Nasal insertion has the advantage of avoiding some of the areas that induce a gagging response in patients.

Oral insertion has the advantage of allowing some direct visualisation of the path followed by the catheter and device and is considered somewhat less invasive. It is more subject to inducing a gag response and more likely to result in unwanted movement of the catheter and device once it is placed.

International patent publication No WO 2006/024825 Hamdy discloses a device for assisting recovery from dysphagia including a catheter for insertion into the body of a patient via the mouth or nose. The catheter comprises electrodes positioned such that when the catheter is in a suitable position within the patient's body, the electrodes are in a position to apply electrical pharyngeal stimulation.

In a further aspect of the present invention there is provided a catheter as described above for use in delivering an electrical stimulus to the body to assist recovery from dysphagia. The catheter comprises a sleeve adapted to move over an elongate shaft, one or more electrodes incorporated into said sleeve, means to fix the sleeve to said elongate shaft once in position and means for connecting said electrodes to a power supply.

When in use for this purpose the sleeve is positioned such that when inserted into a patient the electrodes are in a suitable position for applying electrical pharyngeal stimulation. In a further aspect the catheter may comprise a means to facilitate correct positioning of the electrodes in the form of a diagnostic sensor such as a pressure sensor. The sensor may be included in the sleeve or the elongate shaft. The pressure sensor may be for the measurement of the high pressure zone in the upper oesophagus sphincter of the patient.

The catheter may comprise a means to confirm correct positioning of the catheter and/or the electrodes in the form of a pH sensor. Ideally, the pH sensor is incorporated into the elongate shaft and may be used for the measurement of stomach pH, thus the sensor may be at or near the distal end of the elongate shaft. PH sensors such as those described in EP 2023881 may be particularly suitable for determining that the distal end of the elongate shaft (NG tube) of a pharyngeal stimulation catheter according to the present invention is located in the stomach.

Catheters incorporating a pressure sensor for measurement of the high pressure zone in the upper oesophagus sphincter of the patient or a pH sensor are particularly useful for treating chronic dysphagia.

Ideally a pharyngeal stimulation catheter according to the present invention incorporates a position indicator and a sensor that provides diagnostic information to facilitate correct positioning of the electrodes.

A further aspect of the invention includes a method of assisting recovery from dysphagia, comprising delivering an electrical stimulus to the body comprising sliding a sleeve over the elongate shaft of a catheter, said sleeve comprising one or more electrodes, fixing the sleeve to said elongate shaft once in position, and delivering an electrical stimulus to the body through said electrodes said electrical stimulus capable of inducing pharyngeal stimulation.

As will be apparent to the skilled man, the method may include sliding the sleeve over the elongate shaft of the catheter, adjusting the position of the sleeve and/or elongate shaft, fixing the sleeve to the elongate shaft and then inserting the catheter into the body. The position of the sleeve and/or shaft may, optionally, be further adjusted prior to delivering an electrical stimulus to the body.

Alternatively the sleeve is inserted into the body, followed by the elongate shaft, the position of the sleeve and/or shaft may, optionally, be adjusted after insertion.

In a preferred embodiment of the invention there is provided a method of delivering an electrical stimulus to the body comprising sliding a sleeve over the elongate shaft of a catheter, said sleeve comprising one or more electrodes, clipping the sleeve to said elongate shaft once in position, inserting the device into the appropriate part of the body and delivering an electrical stimulus through said electrodes.

The invention also provides a method of removing a slidable sleeve over a catheter, said sleeve comprising one or more electrodes and a means of fixing said sleeve to said catheter, comprising unclipping the clipping means and sliding said sleeve over said catheter whilst leaving said catheter in situ.

Specific embodiments of the present invention will now be described, by way of example only, with reference to the accompanying drawings.

BRIEF DESCRIPTION OF THE DRAWINGS

FIG. 5 show a connector attached to the proximal end of the sleeve. The connector is in the form of a Y-connector that incorporates a reversible fixing means in the form of a collet that grips the elongate shaft (NG tube).

FIG. 6 shows a Y-connector attached to the proximal end of the sleeve. The Y-connector incorporates a reversible fixing means in a wave form that grips the elongate shaft (NG tube).

FIG. 7 shows a Y-connector attached to the proximal end of the sleeve. The Y-connector incorporates a reversible fixing means in the form of interference ribs that grip the elongate shaft (NG tube).

FIG. 8 shows a Y-connector attached to the proximal end of the sleeve. The Y-connector incorporates a reversible fixing means in the form of a clamshell case that engages with a slidable compliant grommet mounted on the elongate shaft (NG tube).

DETAILED DESCRIPTION

Figure 1:
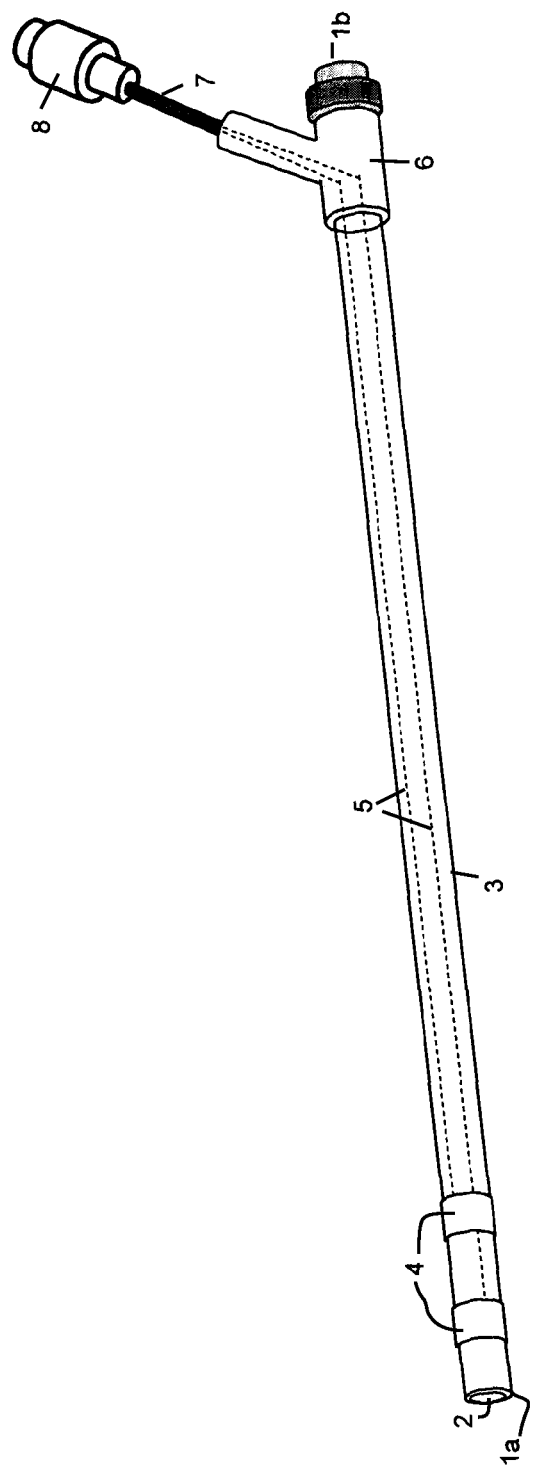
FIG. 1 shows a single sleeve incorporating a pair of electrodes, wires, a Y-connector, a clip and an electrical supply connector.

A first particular preferred embodiment of the invention is for the delivery of electrical pharyngeal stimulation to the oropharyngeal region for the treatment of acute dysphagia in combination with the ability to safely deliver nutrition to the stomach. In this embodiment the core structure (elongate shaft) is a nasogastric (NG) feeding tube, typically 8Fr in diameter and 125 cm or more in length, formed of polyurethane, PVC or silicone, radio-opaque, surface printed at 1 cm distance intervals, terminating at the distal end in one or more feeding ports and at the proximal end with connectors suitable for engagement with an enteral feeding set. The sleeve is preferably a transparent flexible cover made of polyurethane or equivalent material, typically 14Fr in diameter and 35-45 cm in length, incorporating a pair of ring electrodes, wires connected to the electrodes for the delivery of electrical current and a Y-connector to guide the wires to a suitable electrical connector. In addition the invention comprises a clip for fixing the position of the sleeve relative to the NG tube and a means for sealing the gap between sleeve and NG tube at the proximal end of the sleeve. When not fixed in position via the clip the sleeve is capable of freely moving along the length of the core elongate structure. The clip or seal may form a part of the Y-connector assembly and therefore part of the sleeve or may be a feature independent of but connectable to the Y-connector.

In this embodiment the connector at the proximal end of the NG tube may be capable of being disconnected to allow the sleeve to be completely removed by sliding over the proximal end of the NG tube before replacement of the NG connector.

The connector could be configured for easy removal and reattachment to the NG tube in a number of ways including a reversibly engageable clip capable of gripping the NG tube, for example by virtue of ridges or equivalent on its inner surface. It could also operate in a similar fashion to a Touhy-Borst valve whereby NG connector contains a deformable O-ring which can be reversibly compressed through rotation of a screw fit portion and in this way hold or release the tubing which runs through the centre of the O-ring.

The sleeve is a flexible elongate tube generally formed from a plastic material such as polyurethane by a process of extrusion with distal (1*a*) and proximal 1*b*) ends and with a bore (2) extending along its length. The sleeve has a smooth or substantially circular outer surface (3) with at least one electrode, sensor or transducer disposed thereon. If the sleeve is used for the delivery of electrical stimulation, as in the embodiment illustrated in FIGS. 1 and 2, generally there is at least one pair of electrodes (4) positioned on the surface of the sleeve at a location suitable for delivery of such stimulus to the patient. The electrodes are connected to two conducting elements (5) which are disposed laterally within the walls of elongate tube and emerge from the walls via small formed apertures into a Y-shaped junction (6) and from there via an insulated cover (7) to an electrical connector (8). The conducting elements are preferably constructed from multi-strand wire such as steel multi-strand wire. A connection between the electrodes and conducting element (5) is made by removing a section of the sleeve to form apertures exposing the underlying conductive element. The wire may then be bent back and a ring of conductive material applied using conductive adhesive, melting or welding.

The sleeve has an aperture at both the distal (1*a*) and proximal (1*b*) ends in connection with the bore allowing the insertion of elongate shaft and the free movement of the sleeve along the length of the shaft.

Figure 3:
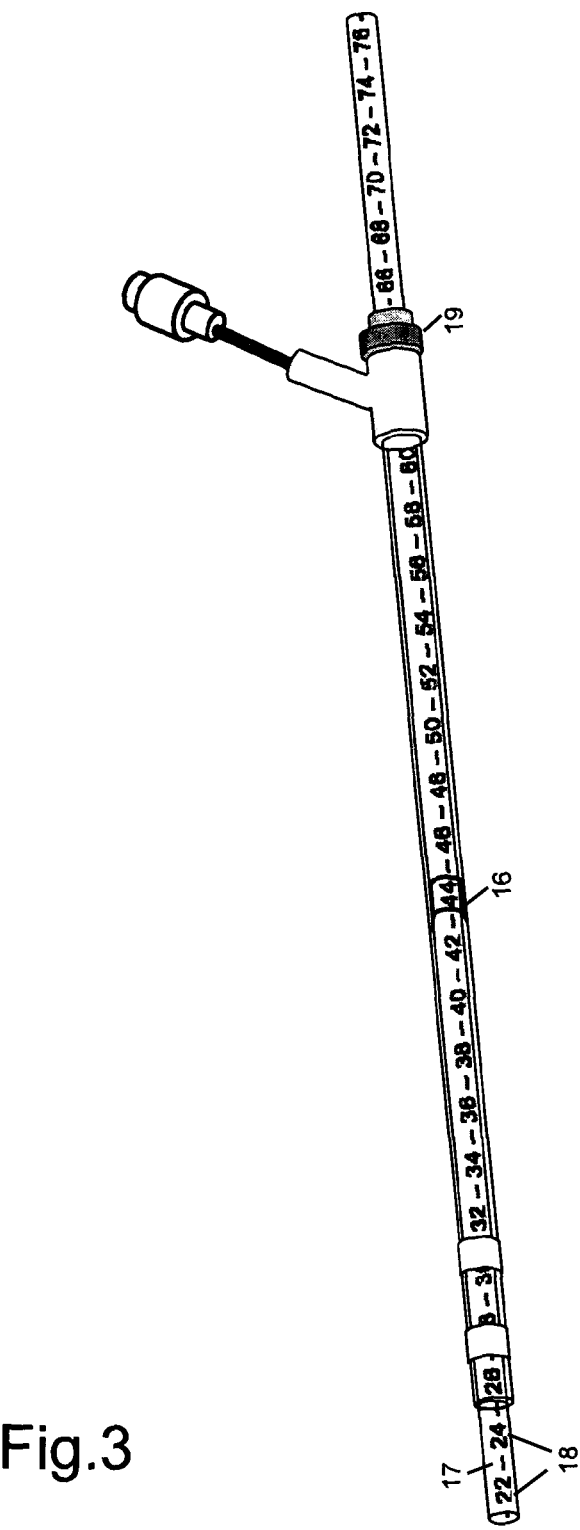
FIG. 3 shows a detail of the sleeve whereby a printed guide or window on the surface of the sleeve can be aligned with marks or guides on the surface of the core elongate structure on which the sleeve is positioned.

As shown in FIG. 3 the sleeve has one or more guides or windows printed or otherwise marked on its surface (16) to allow it to be positioned in a controlled way relative to the core elongated structure (17) and with reference to marks or guides (18) printed on the surface of the core elongate structure.

The sleeve is compatible with the use of a clip (19), which reversibly fixes the sleeve to the core elongate structure once it has been adjusted to the correct position relative to that structure. The clip may be an integral part of the sleeve or may be a separate component. In addition to reversibly fixing the sleeve to the core structure the clip forms a seal to prevent ingress of liquids or particulate matter into the space between sleeve and core structure.

Figure 2:
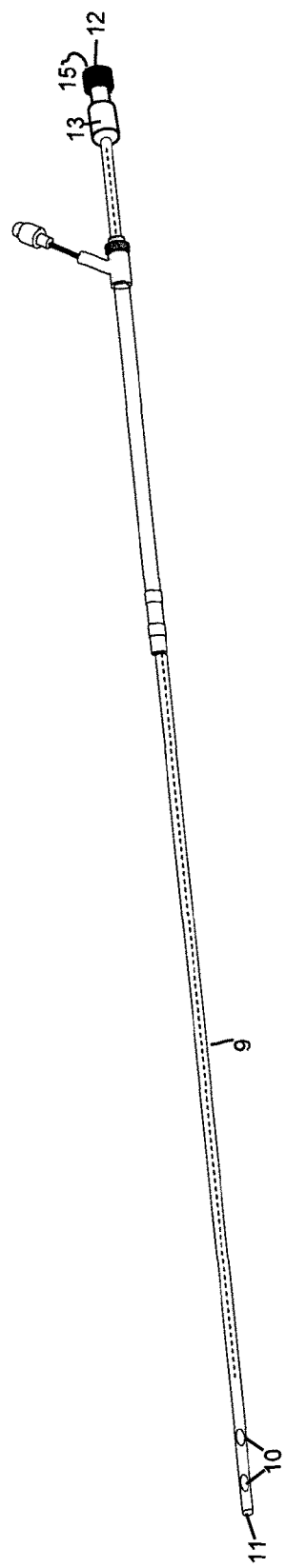
FIG. 2 shows a catheter comprising a sleeve as in FIG. 1 movably positioned over a nasogastric feeding tube.

A catheter according to the present invention, particularly such as that shown in FIG. 2 is useful in a method for the treatment of acute dysphagia, such a method is described in detail below and involves:

Measuring the insertion distance for the core NG tube component by placing the distal end of the NG tube at the entrance to the patient nasal passageway, measuring the tube length to the earlobe and then to the xyphisternum. The total distance figure being noted on the printed guide on the NG tube surface.

Disengaging the fixing clip on the sleeve if necessary and moving the sleeve along the surface of the NG tube until the appropriate window on the surface of the transparent sleeve is lined up over the previously noted insertion distance number. Engaging the fixing clip to prevent independent movement of the sleeve and introducing the catheter either orally or nasally but preferably nasally until the window over the correct insertion distance is just visible at the entrance to the patients' nasal passageways.

Confirming that the distal end of the NG tube component is in the patient stomach is via standard methods namely X-ray or aspiration of stomach contents and testing of the pH.

Delivering nutrition via the core NG tube by connecting to conventional enteral feeding apparatus.

Delivering therapeutic electrical stimulation by connecting an appropriate device to the electrical supply connector on the sleeve and delivering the treatment via the electrodes in the sleeve.

Disengaging the fixing clip and adjustment of the sleeve without removal of the whole catheter assembly from the patient if required.

Disengaging the fixing clip and removal of the sleeve after the treatment regime is finished but without removal of the NG tube.

Disengaging the fixing clip and removing the NG tube without removing the sleeve from the patient if required and introduction of a new NG tube through the body of the sleeve until the correct insertion distance number is lined up with the window of the sleeve and engaging the fixing clip.

In the first embodiment shown in FIG. 2 a catheter is described which has the dual functions of therapeutic electrical stimulation to treat acute dysphagia and delivery of enteral nutrition.

It comprises a core elongate structure in the form of a custom nasogastric (NG) feeding tube (9) onto which is disposed a sleeve capable of freely moving along the length of the NG tube. The sleeve is a substantially transparent flexible tube made of polyurethane, PVC, polyamide, silicone or equivalent material, typically 4.7 mm in outer diameter, with an internal lumen 3.3 mm diameter and 35-45 cm in length, incorporating a pair of ring electrodes, conducting elements disposed laterally along the walls of the tube connected to the electrodes and a Y-connector to guide the wires to an electrical connector. The internal surface of the sleeve may be modified with respect to its hardness, shape, finish or coating such that the modification helps to minimise friction when the sleeve is placed or moved along the NG tube on which it is positioned. The sleeve has visual position indicator in the form of a printed guide or window on its surface to facilitate it's positioning relative to the NG tube and is compatible with the use of a fixing clip to secure the sleeve to the NG tube when required The NG tube is preferably 2.9 mm in diameter, with an internal lumen of 1.9 mm in diameter, 125 cm in length, formed of polyurethane, silicone or equivalent material with one or more ports (10) at its distal end (11) through which nutrients can be passed into the stomach. At its proximal end (12) there is a connector (13) compatible with connection to an enteral feeding set. This connector additionally has the capacity to be removed completely from the NG tube when required such that when removed the sleeve can be separated from the NG tube by sliding over the proximal end of the NG tube. The removable enteral connector can also then be replaced such that the device can continue to be used for enteral feeding purposes thereafter. The external surface of the NG tube may be modified with respect to its hardness, shape, finish or coating such that the modification helps to minimise friction between it and the surface of the internal lumen of the sleeve. The NG tube has a guide in centimeters displaying the distance from the distal end printed on its surface. The NG tube may also incorporate a guidewire (14) positioned within the internal lumen running from the proximal end of the NG tube to a position 1-3 cm from the distal end of the NG tube and fixed to a connector (15) compatible with the enteral connector.

The use of the device will now be described with reference to FIGS. 1 and 2.

The distal end (11) of the NG tube is positioned adjacent to the external nostril of the patient. Whilst keeping the position of the end of the tube next to the nostril the tube is used to measure out the distance to the patients' earlobe and then to their xyphisternum. The total distance in centimeters from nostril to earlobe to xyphisternum (NEX) is obtained from the numerical printed guide on the surface of the NG tube. This represents the correct insertion distance for the NG tube ensuring that when the noted figure is visible at the entrance to the nostril sufficient tube has been inserted to allow the distal end to be within the stomach.

The sleeve is positioned on the NG tube by insertion of the distal end (11) of the NG tube into the proximal end (1a) of the sleeve and pushing it through the bore of the sleeve until it emerges from the distal end (1b) of the sleeve. The sleeve is moved along the surface of the NG tube until the printed window on the sleeve aligns with the insertion distance figure on the printed guide on the NG tube. The sleeve is fixed to the NG tube using the clip on the Y-connector. This ensures that when the combined device is inserted nasally into the patient and the printed window is visible at the entrance to the nostril, sufficient tube has been inserted both to allow the distal end of the NG tube to be within the stomach and to ensure that the electrodes on the sleeve are located within the stimulation target region in the oropharynx. The relative position of the sleeve on the NG tube may vary by 25 cm or more from patient to patient.

The device is inserted nasally into the patient until the printed window on the sleeve is visible at the entrance to the nostril. The guidewire is removed and the section of the device external to the patient secured in position. The correct position of the distal end of the NG tube in the stomach is confirmed by pH testing of stomach aspirate or by X-ray. The enteral feeding connector (13) may be connected to an enteral feeding set to allow nutrient delivery.

Therapeutic electrical stimulation is achieved by connecting an appropriate device to the electrical supply connector on the sleeve and delivering the treatment via the electrodes in the sleeve. In the event that adequate contact between electrodes and target tissues cannot be obtained the clip (19) securing the sleeve to the NG tube may be disengaged and small adjustments made to the vertical position of the sleeve before reengaging the clip. The patient will preferably receive 10 minutes of stimulation at 75% of the maximum tolerated current level at a frequency of 5 Hz and a pulse width of 200 pS for a period of 10 minutes once per day for three consecutive days. In the event that the NG tube becomes irredeemably blocked the clip may be disengaged and the NG tube removed completely whilst keeping the sleeve in place. A new NG tube may then be inserted until the NEX figure is lined up in the printed window of the sleeve and pH testing and X-ray carried out to confirm presence of the distal end in the stomach.

Once the therapeutic electrical stimulation treatment regime is complete it may be desirable to remove the sleeve without removal of the NG tube. This is achieved as follows.

The NEX number on the surface of the NG tube visible through the printed window of the sleeve is noted. The clip securing the sleeve to the NG tube is disengaged and, holding the sleeve to prevent its movement, additional NG tube is inserted through the sleeve into the patient until a figure equal to NEX+20 cm appears in the printed window of the sleeve. The clip is then reengaged.

Both sleeve and NG are then slowly removed until the distal end of sleeve emerges from the nostril and the original NEX number is visible at the entrance to the nostril. This ensures that the distal end of the NG tube is still in the stomach.

If the patient is in the process of receiving enteral feed, the pump is switched off and the enteral feeding connector disconnected from the enteral feeding set. The enteral feeding connector is then detached from the NG tube, the clip securing the sleeve to NG tube disengaged and the sleeve removed from the NG by sliding it over the proximal end of the NG tube. External parts of NG tube are wiped down with an appropriate disinfectant wipe.

The enteral connector is re-attached to the proximal end of the NG tube and then to the enteral feeding set such that feeding can be re-started as required.

Figure 4A:
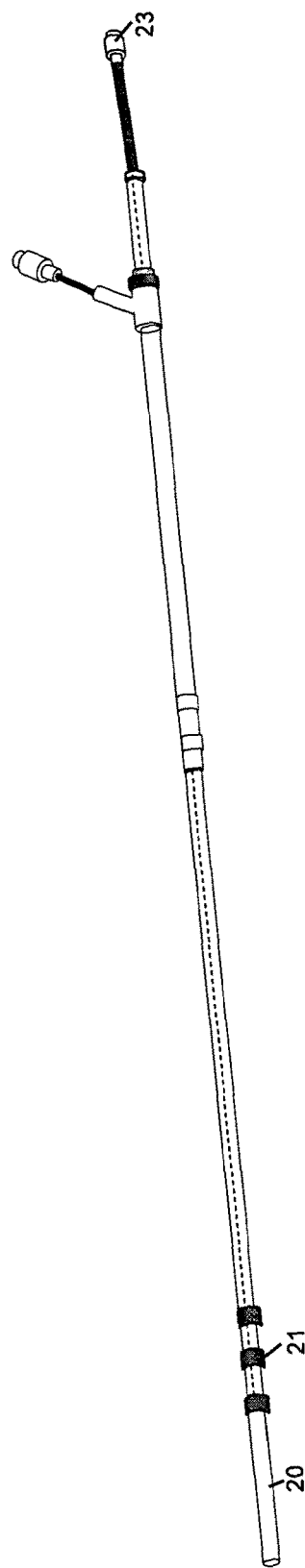
FIGS. 4a and 4b show a catheter comprising a sleeve as in FIG. 1 movably positioned over an elongate tube containing sensors for the measurement of physiological status or function.
Figure 4B:
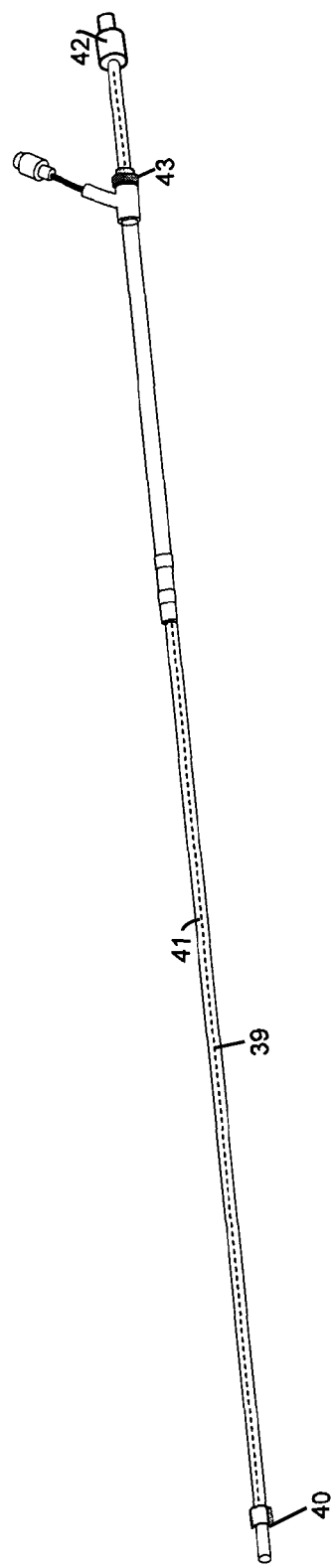

In a second embodiment shown in FIGS. 4a and 4b the device has the dual functions of electrical pharyngeal stimulation and measurement. It comprises a core elongate structure (9) onto which is disposed a sleeve capable of freely moving along the length of the catheter. The sleeve is a substantially transparent flexible tube made of polyurethane, PVC, polyamide, silicone or equivalent material, typically 4.7 mm in outer diameter, with an internal lumen 3.3 mm diameter and 35-45 cm in length, incorporating a pair of ring electrodes, conducting elements disposed laterally along the walls of the tube connected to the electrodes and a Y-connector to guide the wires to an electrical connector. The internal surface of the sleeve may be modified with respect to its hardness, shape, finish or coating such that the modification helps to minimise friction when the sleeve is placed or moved along the catheter on which it is positioned. The sleeve has a printed guide or window on its surface to facilitate its positioning relative to the core elongate structure. More than one window may be printed on the surface to facilitate either nasal or oral insertion of the catheter. The sleeve is compatible with the use of a fixing clip to secure the sleeve to the core structure when required.

The core elongate structure (shaft) can take a number of forms. In one embodiment (FIG. 4a) it comprises a flexible tube typically 8Fr in diameter (20) and 50-70 cm in length, in a region near to its distal end sensors or other means to measure pressure (21) particularly pressure exerted by the action of the upper oesophageal sphincter, within the body of the tube wires to connect to the pressure sensing means (22) and at its proximal end an electrical connector (23) to a suitable means for capturing processing and displaying pressure data.

Figure 5:
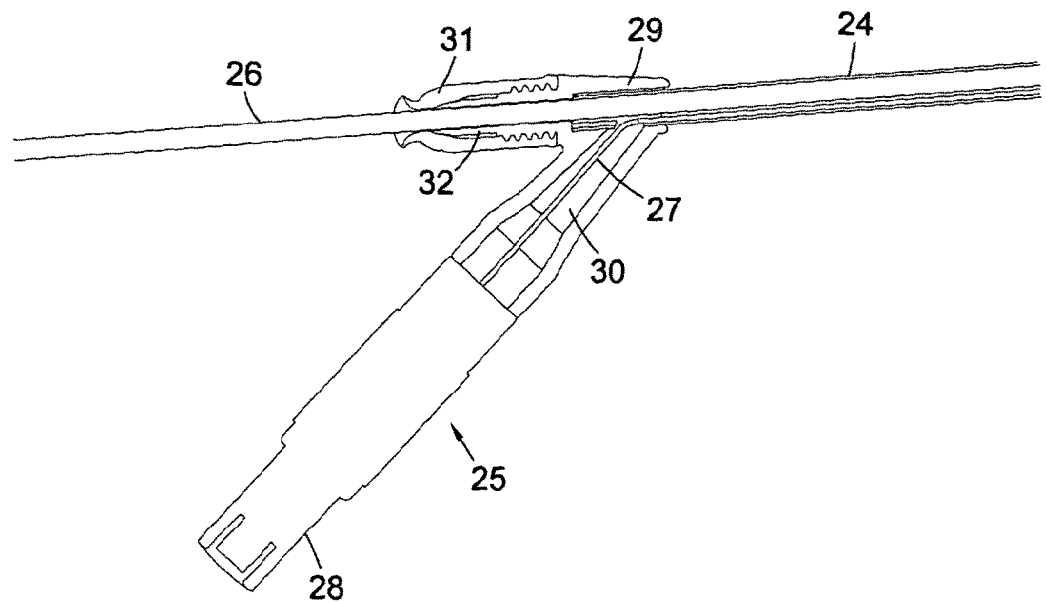
FIGS. 5 to 8 show various configurations of catheter comprising a reversible fixing means incorporated into a connector.

FIG. 5 shows a sleeve (24) having a connector in the form of a Y-connector (25) that incorporates a reversible fixing means in the form of a collet that grips the elongate shaft (NG tube) (26) and also functions to guide the wires (27) to a suitable electrical connector (28). The proximal end of the sleeve (24) is bonded into the proximal end of the Y-connector (29) by gluing, welding, over moulding or the like. The electrode wires (27) from the sleeve break out into a channel (30) in the connector to the electrical connector portion (28). An EEPROM device may be incorporated in the connector. The reversible fixing means comprises a two piece collet device (31) (32), comprising a first piece (31) that can be adjusted by the user to grip or release the NG tube thus permitting the user to easily adjust the sleeve position relative to the NG tube position. The electrical connector portion of the Y-connector may incorporate a sealing mechanism e.g. cap (not shown) for infection control purposes, the cap is used to seal the electrical connector when the electrical stimulation function is not in use.

Figure 6:
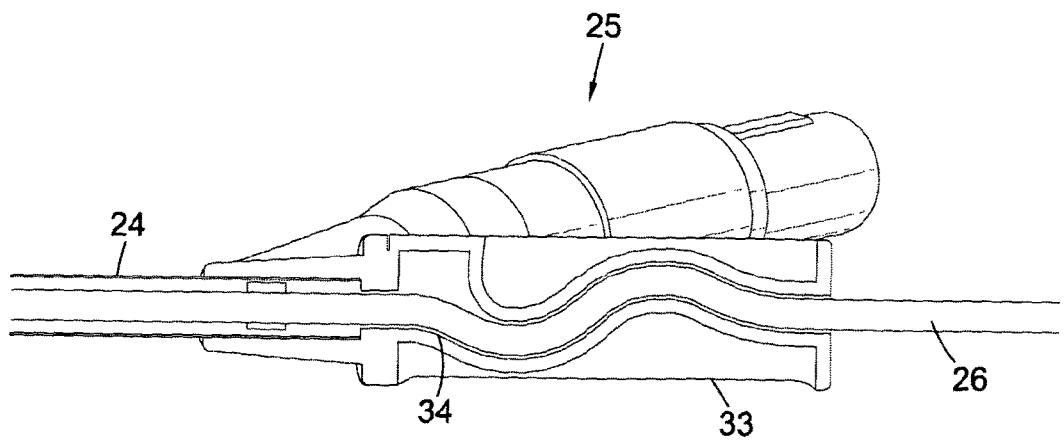

FIG. 6 shows a Y-connector attached to the proximal end of the sleeve (24), The Y-connector incorporates a reversible fixing means in the form of a casing (33) that incorporates a "wave form" (34) that grips the elongate shaft (NG tube). The position of the sleeve relative to the NG tube is adjusted by the user and fixed by the user inserting the NG tube into the wave form channel (34) and closing the casing (not shown).

Figure 7:
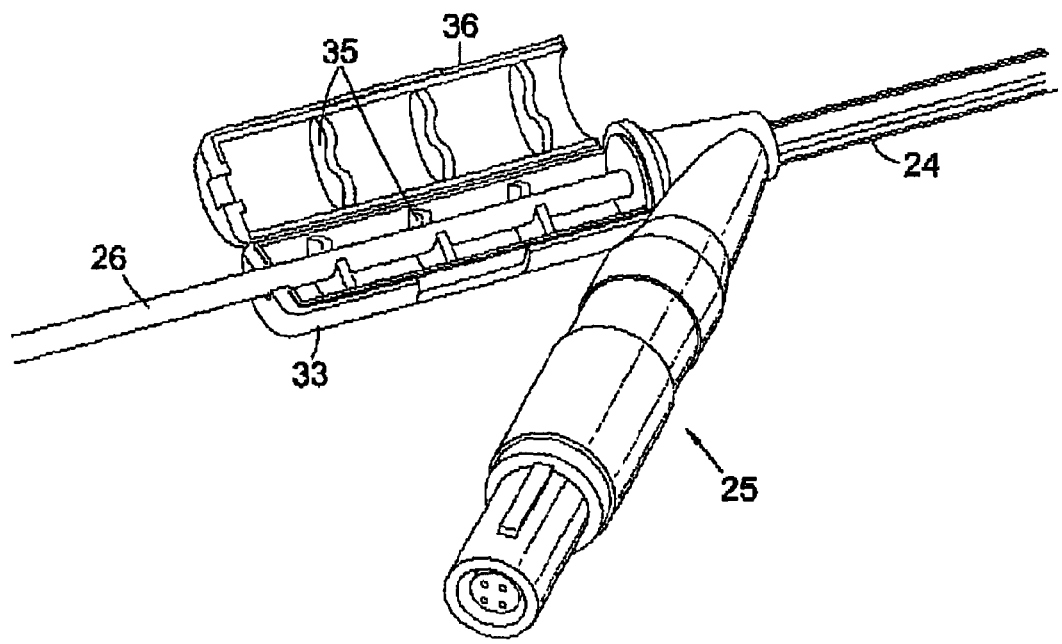

FIG. 7 shows a Y-connector (25) attached to the proximal end of the sleeve (24). The Y-connector incorporates a reversible fixing means in the form of casing (33) having interference ribs (35) that engage the elongate shaft (NG tube) (26), the interference ribs create a labyrinth that locks the NG tube in place. The user may easily adjust the sleeve position relative to the NG tube position and then fix the position by closing the lid (36) of the casing.

Figure 8:
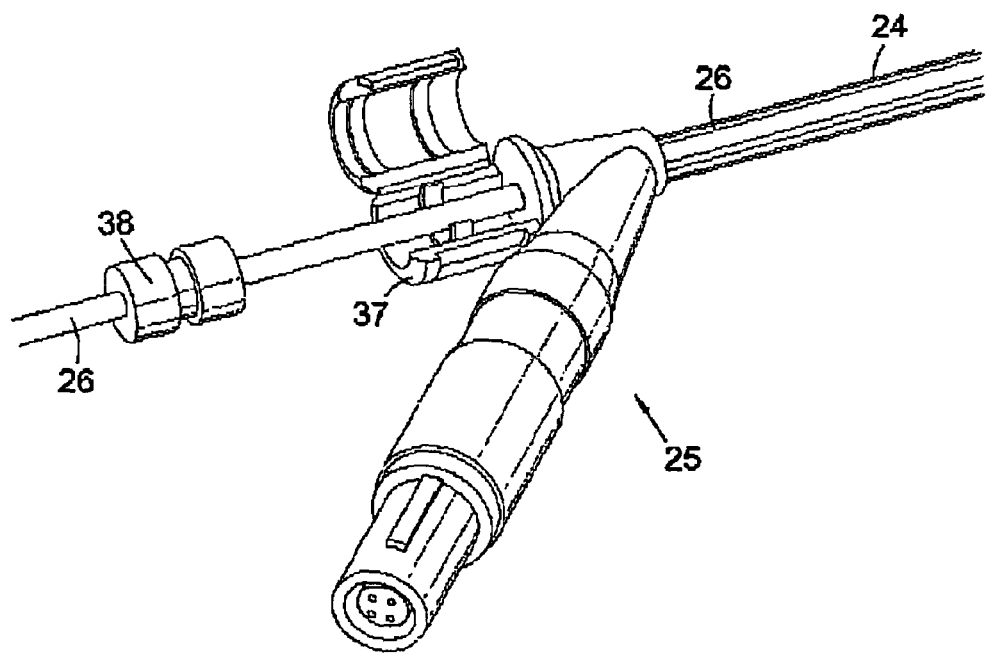

FIG. 8 shows a Y-connector (25) attached to the proximal end of the sleeve (24). The Y-connector incorporates a reversible fixing means in the form of a clamshell case (37) that engages with a slidable compliant grommet (38) mounted on the elongate shaft (NG tube) (26). The grommet may be made of suitable materials such as deformable silicone or the like so that there is friction between the polyurethane NG tube and the grommet.

The invention includes a method for the treatment of acute dysphagia, comprising;

Measuring the insertion distance for the core NG tube component by placing the distal end of the NG tube at the entrance to the patient nasal passageway, measuring the tube length to the earlobe and then to the xyphisternum. The total distance figure being noted on the printed guide on the NG tube surface.

Disengaging the fixing clip on the sleeve if necessary and moving the sleeve along the surface of the NG tube until the appropriate window on the surface of the transparent sleeve is lined up over the previously noted insertion distance number.

Engaging the fixing clip to prevent independent movement of the sleeve and introducing the catheter either orally or nasally but preferably nasally until the window over the correct insertion distance is just visible at the entrance to the patients' nasal passageways.

Confirming that the distal end of the NG tube component is in the patient stomach is via standard methods namely X-ray or aspiration of stomach contents and testing of the pH.

Delivering nutrition via the core NG tube by connecting to conventional enteral feeding apparatus. Delivering therapeutic electrical stimulation by connecting an appropriate device to the electrical supply connector on the sleeve and delivering the treatment via the electrodes in the sleeve.

Disengaging the fixing clip and adjustment of the sleeve without removal of the whole catheter assembly from the patient if required.

Disengaging the fixing clip and removal of the sleeve after the treatment regime is finished but without removal of the NG tube.

Disengaging the fixing clip and removing the NG tube without removing the sleeve from the patient if required and introduction of a new NG tube through the body of the sleeve until the correct insertion distance number is lined up with the window of the sleeve and engaging the fixing clip.

The use of this embodiment of the device will now be described with reference to FIGS. 1 and 4a.

The sleeve is positioned on the core elongate structure by insertion of the distal end (11) of the core structure into the proximal end (1a) of the sleeve and pushing it through the bore of the sleeve until it emerges from the distal end (1b) of the sleeve. The sleeve is moved along the surface of the core structure until the printed window on the sleeve aligns either with a mark on the core structure corresponding to the average distance from the eternal entrance to the nostril to the centre of the upper oesophageal sphincter or a mark corresponding to the average distance from the incisors to the centre of the upper oesophageal sphincter, depending on whether the device is to be inserted nasally or orally. The sleeve is fixed to the core structure using the clip on the Y-connector. This ensures that when the combined device is inserted nasally or orally into the patient and the printed window is visible at the entrance to the nostril or incisors, sufficient tube has been inserted both to allow one or more of the pressure sensors located in distal region of the core structure to be close to or within the upper oesophageal sphincter whilst at the same time ensuring that the electrodes on the sleeve are located within the stimulation target region in the oropharynx.

The electrical connector on the proximal end of the core structure (23) is connected to a suitable means for analysing and displaying pressure measurements from the pressure sensors in the distal region of the catheter. The combined sleeve and core structure are inserted either nasally or orally until the printed window is approximately 5 cm from the entrance to the nostril or incisors. The means for displaying pressure measurements is then monitored whilst continuing to insert the device. A characteristic change in the pressure readings indicates that the pressure sensors are within the upper oesophageal sphincter and that the distal end of the core structure is located within the oesophagus and not the upper airways. If required the device is further inserted until such time as the printed window on the surface of the sleeve is located at the entrance to the nostril or incisors as appropriate. The part of the device external to the patient is secured in position to prevent unwanted movement.

Therapeutic electrical stimulation is achieved by connecting an appropriate device to the electrical supply connector on the sleeve and delivering the treatment via the electrodes in the sleeve. In the event that adequate contact between electrodes and target tissues cannot be obtained the clip (19) securing the sleeve to the core structure may be disengaged and small adjustments made to the vertical position of the sleeve before reengaging the clip.

On completion of treatment the combined sleeve and core structure are removed slowly from the patient. The clip securing the sleeve to the core structure is disengaged and the sleeve removed by sliding it off the distal end of the catheter. Subsequent treatments to complete the treatment regime employ a new single use sterile sleeve each time. The core structure may be disposable or reusable. In the latter case the core structure is sterilised between treatments by standard methods known in the art.

In the embodiment shown in FIG. 4b the core elongate structure comprises a flexible tube typically 8Fr in diameter (39) and 125 cm in length, in a region near to its distal end sensors or other means to measure pH (40) particularly low pH values consistent with the distal end of the elongate structure being positioned within the stomach, within the body of the tube wires to connect to the pH sensing means (41), a guide in centimeters displaying the distance from the distal end printed on its surface and at its proximal end a connector (42) to a suitable means for capturing, processing and displaying pH data.

The use of this embodiment of the device will now be described with reference to FIGS. 1 and 4b.

The distal end of the core structure is positioned adjacent to the external nostril of the patient. Whilst keeping the position of the end next to the nostril the core structure is used to measure out the distance to the patients' earlobe and then to their xyphisternum. The total distance in centimeters from nostril to earlobe to xyphisternum (NEX) is obtained from the numerical printed guide on the surface of the core structure. This represents the correct insertion distance for the core structure to ensure that when the noted figure is visible at the entrance to the nostril sufficient tube has been inserted to allow the distal end to be within the stomach.

The sleeve is positioned on the core structure by insertion of the distal end of the core structure into the proximal end (1a) of the sleeve and pushing it through the bore of the sleeve until it emerges from the distal end (1b) of the sleeve. The sleeve is moved along the surface of the core structure until the appropriate printed window (depending on whether the catheter is to be inserted orally or nasally) on the sleeve aligns with the NEX number. The sleeve is fixed to the catheter using the clip on the Y-connector. This ensures that when the combined device is inserted nasally or orally into the patient and the printed window is visible at the entrance to the nostril or incisors, sufficient tube has been inserted both to ensure the distal end of the catheter will be in the patients' stomach whilst at the same time ensuring that the electrodes on the sleeve are located within the stimulation target region in the oropharynx.

The combined sleeve and catheter are inserted either nasally or orally until the printed window positioned at the entrance to the nostril or incisors. The connector on the proximal end of the catheter (42) is connected to a suitable means for analysing and displaying pH measurements from the pH sensors in the distal region of the catheter. A pH reading of 5.5 or less is indicative that the distal end of the core structure is located within the stomach and not the airways. The part of the device external to the patient is secured in position to prevent unwanted movement.

Therapeutic electrical stimulation is achieved by connecting an appropriate device to the electrical supply connector on the sleeve and delivering the treatment via the electrodes in the sleeve. In the event that adequate contact between electrodes and target tissues cannot be obtained the clip (43) securing the sleeve to the core structure may be disengaged and small adjustments made to the vertical position of the sleeve before reengaging the clip.

On completion of treatment the combined sleeve and core structure are removed slowly from the patient. The clip securing the sleeve to the catheter is disengaged and the sleeve removed by sliding it off the distal end of the core structure. Subsequent treatments to complete the treatment regime employ a new single use sterile sleeve each time. The core structure may be disposable or reusable. In the latter case the core structure is sterilised between treatments by standard methods known in the art.

What is claimed is:

1. A pharyngeal stimulation catheter for delivering an electrical stimulus to a body to assist recovery from dysphagia, comprising:
   i) an elongate shaft having a position indicator;
   ii) a sleeve incorporating one or more electrodes, the sleeve being sized to co-axially surround and be movable along the elongate shaft such that a correct position of the sleeve relative to the elongate shaft is indicated by the position indicator before the catheter is inserted into the body; and
   iii) a releasable fastener which fixes the correct position of the sleeve such that the elongate shaft and the sleeve can be inserted while affixed together in the correct position into the body allowing the elongate shaft to be within a stomach of the body and to ensure the one or more electrodes on the sleeve are located within a stimulation target region in an oropharynx of the body and wherein the elongate shaft is releasable from the sleeve and selectively removable from the body without removal of the sleeve from the body.

2. The catheter as claimed in claim 1 wherein the elongate shaft incorporates at least one therapeutic, feeding or diagnostic function.

3. The catheter as claimed in claim 1, wherein the position indicator is in the form of a visual indicator printed on a surface of the elongate shaft to indicate the relative position of the sleeve.

4. The catheter as claimed in claim 1 wherein the releasable fastener comprises a clip.

5. The catheter as claimed in claim 1 wherein the sleeve has a tubular opening sized to receive the elongate shaft, and the elongate shaft has a tubular cavity sized to coaxially receive the sleeve.

6. The catheter as claimed in claim 1 wherein the releasable fastener is located at a proximal end of the sleeve.

7. The catheter as claimed in claim 1 wherein the releasable fastener forms a seal between the sleeve and elongate shaft.

8. The catheter as claimed in claim 1 wherein the sleeve is dimensioned such that when in an operable position in the body, the sleeve extends to the outside of the body.

9. The catheter as claimed in claim 1 further comprising a conductor connecting the electrodes to a power supply.

10. The catheter as claimed in claim 1 further comprising one or more pressure sensors.

11. The catheter as claimed in claim 10 wherein the pressure sensor is for detecting a high pressure zone in an upper esophagus sphincter of the body.

12. The catheter as claimed in claim 10 wherein the pressure sensor is mounted on the elongate shaft.

13. The catheter as claimed in claim 1 further comprising one or more pH sensors.

14. The catheter as claimed in claim 13 wherein the pH sensor is mounted on the elongate shaft.

15. The catheter as claimed in claim 1 wherein the elongate shaft further comprises an enteral feeding connector.

16. The catheter as claimed in claim 15 wherein the enteral feeding connector is detachable to permit removal of the sleeve.

17. A method of delivering an electrical stimulus to a body to induce pharyngeal stimulation for assisting in recovery from dysphagia using a catheter, the method comprising: sliding a sleeve comprising one or more electrodes over an elongate shaft of the catheter having a position indicator which indicates the relative position of the sleeve and the elongate shaft, fixing the sleeve to the elongate shaft once in a correctly indicated position relative to the elongate shaft prior to inserting the catheter with the sleeve affixed to the elongate shaft into the body, the correct position allowing the elongate shaft to be within a stomach of the body and the one or more electrodes on the sleeve to be located within a stimulation target in an oropharynx of the body, and delivering an electrical stimulus through the electrodes to induce the pharyngeal stimulation.

18. The method according to claim 17 wherein the sleeve is removed following delivery of the electrical stimulus.

* * * * *